United States Patent [19]
Brost et al.

[11] Patent Number: 5,418,614
[45] Date of Patent: May 23, 1995

[54] OPTICAL PHOTOMETRY SYSTEM FOR ON-LINE ANALYSIS OF FLUID SYSTEMS

[75] Inventors: Dale F. Brost, Sugarland; Frank M. Rexach; Gregory A. Winslow, both of Houston, all of Tex.

[73] Assignee: Texaco Inc., White Plains, N.Y.

[21] Appl. No.: 47,990

[22] Filed: Apr. 19, 1993

Related U.S. Application Data

[63] Continuation of Ser. No. 762,287, Sep. 19, 1991, abandoned.

[51] Int. Cl.[6] .................. G01N 21/31; G01N 21/33; G01N 21/35
[52] U.S. Cl. .................. 356/434; 250/227.23; 356/408; 356/411; 356/435; 356/436
[58] Field of Search ............... 356/434, 408, 410, 411, 356/435, 436, 437; 250/227.23

[56] References Cited
U.S. PATENT DOCUMENTS

| | | | |
|---|---|---|---|
| 4,275,295 | 6/1981 | Menningen et al. | 250/901 X |
| 4,753,530 | 6/1988 | Knight et al. | 356/435 X |
| 4,786,171 | 11/1988 | Lefebre et al. | 356/436 X |
| 4,802,768 | 2/1989 | Gifford | 356/417 |
| 5,051,578 | 9/1991 | Slemon et al. | 250/227.23 |

*Primary Examiner*—Vincent P. McGraw
*Attorney, Agent, or Firm*—James L. Bailey; Kenneth R. Priem; William J. Beard

[57] ABSTRACT

The present invention concerns a new optical photometry system for on-line analysis of industrial fluid streams. The invention is a general purpose optical photometer, capable of absorption, fluorescence and reflectance measurements at single wavelengths in the ultraviolet, visible and near infrared spectral ranges. Light signals generated by the light source are carried between a central photometric console and remote analysis sites by fiber optic cables. The return light signals are compared with a standard to make the desired analysis.

12 Claims, 6 Drawing Sheets

OPTICAL PHOTOMETRY SYSTEM FOR ON-LINE ANALYSIS OF FLUID SYSTEMS

This is a continuation of patent application Ser. No. 07/762,287, filed Sep. 19, 1991, now abandoned.

BACKGROUND OF THE INVENTION

1. The Field of the Invention

The present invention relates to an optical photometry system for measuring pulsed light signals from optic probes used in the analysis of industrial fluid streams.

2. The Prior Art

There are a great many industrial processes which include fluid streams and which have need to monitor aspects of the flowing streams. These processes include those that are designed to modify the chemical composition of one or more sources to the streams. For example, chemical synthesis processes convert source streams of chemical reactants into chemical products. A process designed to remove oil or other contaminants from a source water stream is another example. Other types of processes use fluid streams to produce a desired physical environment. An example of this type of process would be a water cooling system designed to reduce the temperature of an internal combustion engine. Although there are many different types of fluid processes, they all are controlled in one way or another by the chemical composition of their fluid streams. Because of this, it is important to monitor the chemical composition of fluid streams in real-time, so that the information can be used to optimize the process's parameters before the process is complete.

There are also a great many processes involving bodies of liquid into which a treating agent is added. Maintaining the proper feed level of the agent can be critical to the optimal performance of many of these processes. For example, severe corrosion and/or deposit formation can occur rapidly on heat-exchange surfaces of cooling and boiling water systems if an incorrect level of treating agent is used. One common method of estimating concentration levels focuses on measuring the level of an active component of the treating agent, such as a polymeric scale inhibitor, phosphate or organophosphonate. This may not always be a suitable method due to background interferences and the bulky, labor intensive equipment which is currently available. A known method for determining the optimum feed rate of a treating agent is described in U.S. Pat. No. 4,783,314, the disclosure of which is incorporated herein by reference.

There are a great many analytical methods for determining the concentration of chemical substances in industrial fluid streams. Many methods are optical in nature; that is, they are based upon the inherent ability of a chemical substance to absorb, emit or reflect light in a manner proportional to its concentration. Chemical additives that do not possess inherent optical properties can nonetheless be determined indirectly by optical techniques if an optical tracer is added to the chemical prior to its addition to a fluid stream. A known method for such an indirect determination, based upon the addition of fluorescent dye to a chemical product, is also described in the above mentioned U.S. Pat. No. 4,783,314.

A variety of optical spectrometers are commercially available for the on-line analysis of industrial fluid streams. Examples of these are the Models 260 and 300 manufactured by Guided Wave, Inc. of El Dorado Hills, Calif. None of these known instruments, however, are designed for long term use in harsh industrial environments. Their light detection systems require continuous beams of light in order to operate. These beams are produced by a variety of continuous light sources which generate large amounts of heat. This results in rapid build-up of heat inside the instrument case and the requirement that such instruments be operated at ambient temperatures not greater than 35° C. Many industrial process sites, especially those in the oil industry, have ambient temperatures in excess of 55° C. Therefore, installation of these know instruments in such an environment would require additional facilities for climate control. In addition, the long-term utility of these known instruments is limited by the myriad of moving parts that are used for wavelength selection and optical multiplexing. The abrasive and corrosive conditions of some industrial environments (e.g. blowing sand and acid gases found in oil producing fields), often lead to the rapid failure of such mechanical devices.

The subject invention improves upon existing commercial optical on-line analysis instruments by providing a general purpose filter photometry system which can be configured for absorption, fluorescence and reflectance measurements in the ultraviolet, visible and near infrared spectral ranges. Conversion from one type of measurement to the other is achieved simply by selecting the appropriate light source, detector and optical probe. The instrument utilizes brief flashes of light which can be generated by a variety of pulsed light sources. Since pulsed light sources can generate extremely high light intensities, without generating correspondingly large amounts of heat, the present invention can be operated at the high ambient temperatures often encountered in industrial environments, while still allowing ultra-low detection limits, as low as parts per trillion for some fluorescent substances. Its pulsed mode of operation also allows light signals from several fiber optic probes to be sequentially monitored by a single photodetector. This is accomplished by flashing the excitation light source for each optical probe in sequence, so that only one signal reaches the detector at any given time. This temporal approach to optical multiplexing is rapid, extremely reproducible, and requires no moving parts. It is a significant improvement over spatial fiber optic multiplexers which are very slow, mechanically complex, and suffer from poor reproducibility. A dual-channel integrator simultaneously measures the light intensity emitted by the pulsed source and the resulting pulsed light intensity from an analytical probe. This allows each flash of the light source to yield an analytical signal that has been corrected for source fluctuations. Instrument performance is therefore not degraded as the pulsed light source becomes more erratic with age. The temporal multiplexing design also allows internal reference signals to be interspersed between analytical probe signals, making it possible to correct instrument response for drifting photodetector sensitivity.

SUMMARY OF THE INVENTION

The present invention concerns an optical photometry system for on-line analysis of fluid systems having at least one excitation and one reference light source, having substantially identical light sensitivities and temperature coefficients, means controlling the light sources to flash in timed sequence, photodetector means for sensing the output of each light source, and optical fiber means coupling the output from the excitation light source to a probe inserted into the fluid to be analyzed,- coupling light sensed by the probe to the photodetector means, and coupling the output from the reference light source to the photomultiplier means whereby a combination of the light signals is made to analyze the fluid in the system.

BRIEF DESCRIPTION OF THE DRAWINGS

The present invention will be described, by way of example, with reference to the accompanying drawings in which.

DETAILED DESCRIPTION OF THE PREFERRED EMBODIMENT

Figure 1:
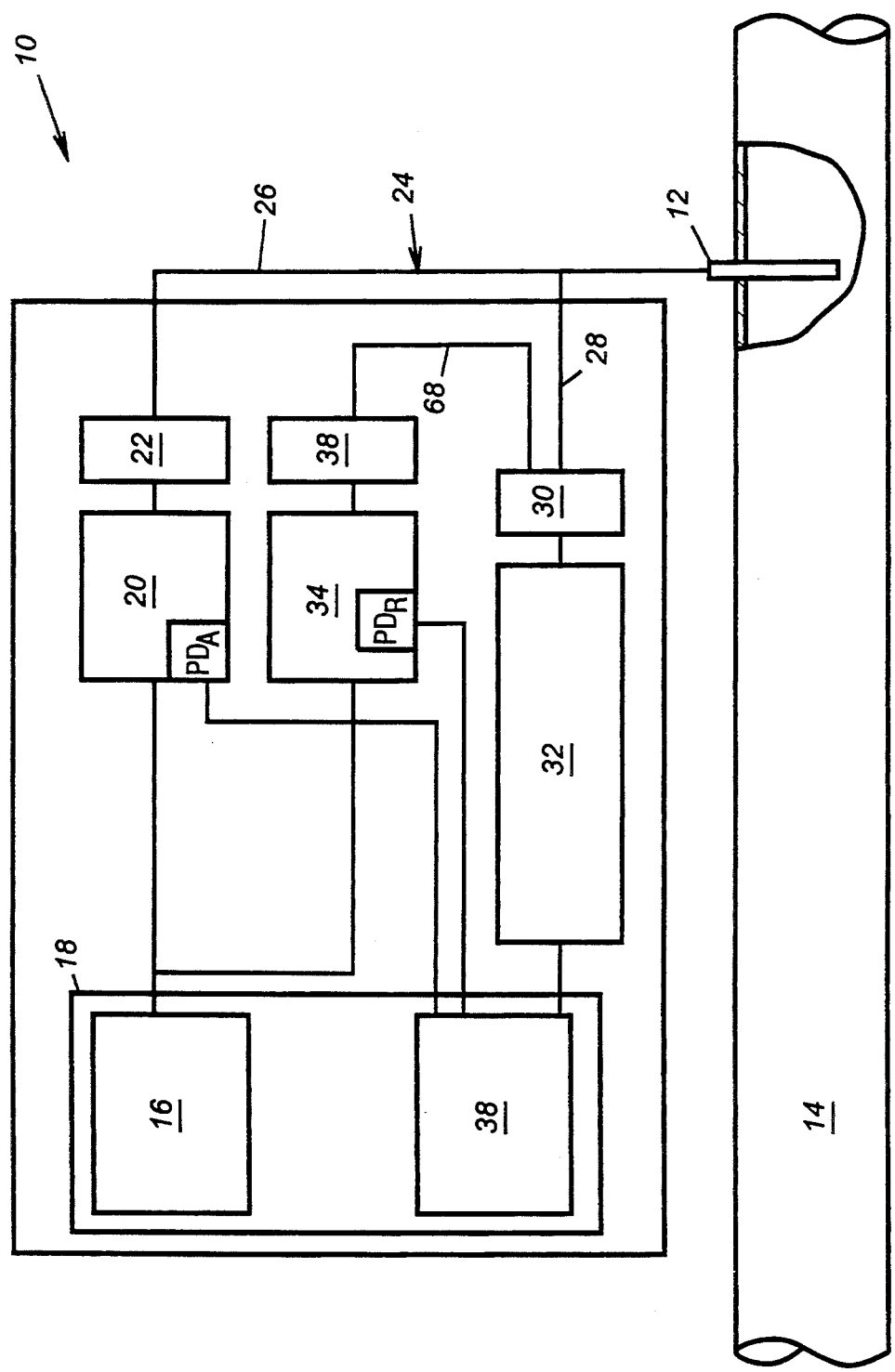
FIG. 1 is a block level schematic of the subject optical photometry system according to the present invention.

The subject optical photometry system 10 is coupled in known fashion to a fiber optic probe 12 which in turn is mounted, in known fashion, to extend into flow pipe 14. The conventional features, such as the probe itself and the various couplings and seals have not been shown for sake of clarity. A microprocessor 16, which is part of computer module 18, is connected to first or excitation light source module 20, which is a known means of producing a momentary pulse of light. The output of light source module 20 passes through filter means 22 and is optically coupled to a fiber optic cable 24, the other end of which is optically coupled to probe 12. The cable 24 has been here shown as a bifricated cable with first leg 26 coupled to the filter means 22 and second leg 28 optically coupled to filter means 30. Other cable configurations could also be used. Light, which has been modified in wavelength and/or intensity by substances in flow pipe 14, is received by probe 12 and passes through the fiber optic cable 24 to filter means 30 and to photodetector 32. The microprocessor 16 is also connected to a second or reference light source module 34. The output of this second light source module 34 is coupled through filter means 36 and filter means 30 to photodetector 32. Pulsed outputs from both light source modules 20 and 34 are converted to time varying electronic signals by signals, along with time varying signals from photodetector 32 are received by a dual-channel integrator 38, which is part of computer module 18.

The subject optical photometry system can be configured with many types of pulsed light sources and photodetectors. These components are chosen by one skilled in the art according to their suitability for a particular type of photometric analysis. Possible light sources include, but are not limited to, xenon flash lamps, pulsed lasers, pulsed diode lasers, and pulsed light emitting diodes, as well as continuous sources that have been pulsed by electronic or mechanical choppers or shutters. Suitable photodetectors are those that respond to the wavelengths of light emitted by the source, and have response times that are less than the period of the source pulse. These include, but are not limited to, avalanche photodiodes, PIN photodiodes, vacuum phototubes and photomultiplier tubes.

In many respects, xenon flash lamps are ideal sources for many types of photometric measurements. Broad band radiation, from the deep ultraviolet to the near infrared, is produced in brief pulses by electronic discharges through pressurized xenon gas. Discharge arcs are small, which accommodates efficient coupling to optical fibers. Output energies are extremely high (up to 0.15 joules per flash), which is excellent for excitation of fluorescent emissions. Flash durations are very short, typically about 4 microseconds. When the flash rate is 5 Hz, the lamp is "ON" only 0.002% of the time, resulting in very little heat generation. This is important for an instrument intended for use at high ambient temperatures. Xenon lamps are rated for more than $10^9$ flashes. When operated at 5 Hz, this translates to a useful life of approximately 6 years.

Returning to the block diagram of FIG. 1, the subject optical photometer 10 is shown configured with one analysis probe 12 inserted into a flow pipe 14. During operation, the microprocessor 16 triggers the analysis or excitation light source module 20 to emit a brief light pulse. The light pulse is filtered by filter means 22 to the wavelength of interest, and is carried to the flow pipe by fiber optic cable 24. After interacting with substances in the fluid system, the residual light is collected by probe 12, and is transmitted to photodetector 32 by fiber optic cable 24. Two analysis signals are simultaneously produced. The first is generated by photodetector $PD_A$, which is positioned to receive part of the output of the first light source 20. This is a time varying signal that is proportional to the light intensity emitted by the source 20 during the flash. The second signal is generated by the photodetector 32, and is a time varying signal that is proportional to the intensity of the light returning from the flow pipe 14 via the analysis probe 12.

Figure 2:
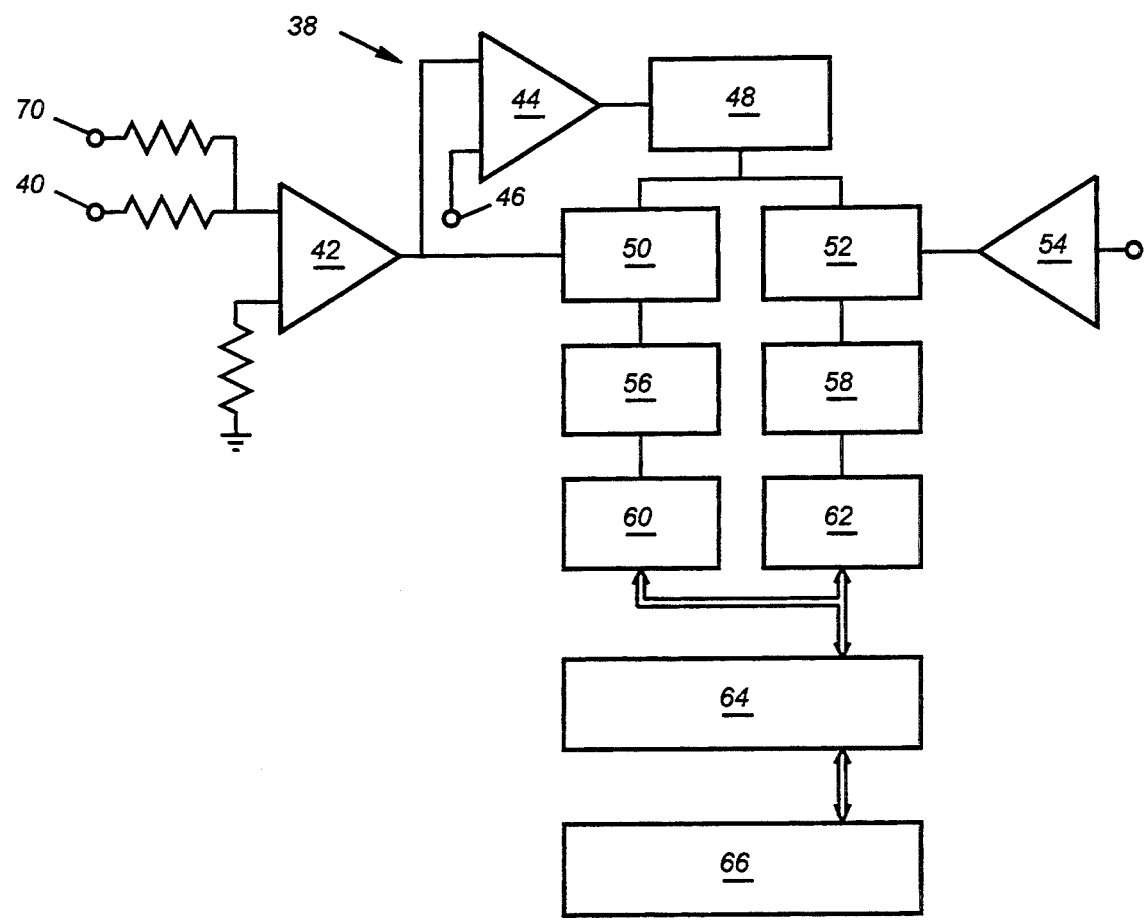
FIG. 2 is block level schematic of a dual channel integrator according to the present invention.

Both analysis signals are processed simultaneously by the dual-channel integrator circuit 38, shown in detail in FIG. 2. The time varying signal from photodetector $PD_A$ enters at 40 and passes through summing input amplifier 42 and is passed to the input of comparator 44. When the leading edge of the source signal exceeds a preset reference voltage at 46, comparator 44 changes state and triggers the integration timer 48, which enables a source signal integrator 50 and a probe signal integrator 52. The latter receives a probe photodetector signal through input amplifier 54. After the signals are integrated for a preset time period, they are stored briefly in sample-and-hold circuits 56 and 58 and are digitized by 12 bit analog-to-digital converters 60 and 66. The analysis data, integrated source intensity, $L_A$, and integrated probe intensity, $P_A$, are then multiplexed onto a computer bus 64 and stored in memory 66 for later processing.

Immediately after collecting the analysis signals, the microprocessor 16 initiates a reference light pulse by triggering reference light source module 34. This reference pulse is attenuated by filter means 36, and passed directly, via a short fiber optic cable 68, to the photodetector 32. Two time varying reference signals are simultaneously produced, one from photodetector 32, and one from photodetector $PD_R$. Both signals are integrated and stored in memory as described above. The signal from photodetector $PD_R$ enters the integrator circuit at 70. Its integrated value, $L_R$, is proportional to the intensity of the reference light source 34. The reference signal from photodetector 32 enters through input amplifier 54. Its integrated value, $P_R$, is also proportional to the output of reference light source 34.

Analysis values $P_A$ and $L_A$ are combined with reference values $P_R$ and $L_R$ according to Equation 1 to yield an analytical response, R, that is independent of light source intensity and photodetector sensitivity.

$$R = P_A L_R / P_R L_A \qquad (1)$$

Equation 1 is valid if photodetectors $PD_A$ and $PD_R$ have the same sensitivity to light and have the same temperature coefficients. Use of R as a response parameter allows the subject photometry system to maintain calibration over long periods of time under widely varying temperature conditions.

Figure 3:
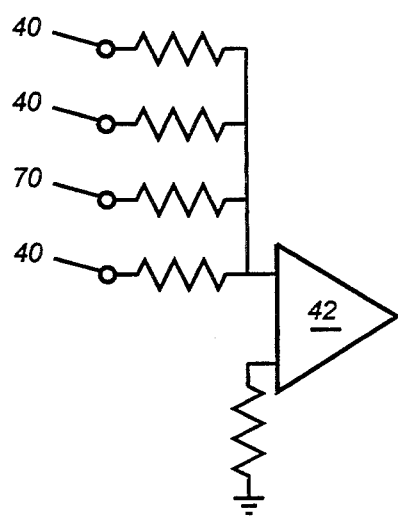
FIG. 3 is a schematic of a representative multiple lamp photodiode input for the subject invention.

The subject photometry system can be configured to process signals from multiple fiber optic probes. This can be accomplished simply by adding more pulsed light source modules (which have not been shown). The microprocessor 16 energizes only one light source at a time, allowing multiple probes to be read by a single detector. Additional light source photodiodes are handled by the dual-channel integrator simply by adding inputs 40', 40" to summing input amplifier 46, as shown in FIG. 3

An example analysis instrument was constructed with one analysis probe. Components were assembled as pictured in FIG. 1. The subject photometry system was configured with light source modules 20 and 34 each consisting of externally triggerable xenon flash lamp power supplies and xenon flash lamps with synthetic silica envelopes. Light source module 20 contained a high power flash lamp power supply and light source module 34 contained a lower power flash lamp power supply. Photodetector 32 consisted of a high temperature photomultiplier tube with a high voltage power supply. Photodetectors $PD_A$ and $PD_R$ were silicon PIN photodiodes. Fiber optic cable 24 consisted of a ⅛" diameter bundle of 200 $\mu$m core Superguide G optical fibers. When coupled with the appropriate fiber optic probe, this configuration allowed absorption, fluorescence and reflectance measurements to be made at single wavelengths in the ultraviolet and visible spectral ranges.

Two types of fiber optic probes were used for lab and field tests of the example instrument. The first was a fluorescence probe consisting of a bifurcated fiber optic cable (as shown in FIG. 1) containing 510 Superguide G optical fibers. The excitation leg 26, which carried light to the flow pipe, contained 40% of the total fibers. The emission leg 28, which carried fluorescent emissions to the photomultiplier, contained the remaining 60%. The common end of the bundle, where the excitation and emission fibers came together, formed probe 12. The second type of analysis probe 12 was a wand-type absorption probe, model 1-1W250-8B by Guided Wave, Inc. of El Dorado Hills, Calif. The probe contained 2 silica optical fibers, each with a core diameter of 500 $\mu$m.

The computer 18 was chosen for IBM-PC compatibility. Application programs were written in "C". A variety of analog and digital interfaces were be included to allow the example instrument to intelligently participate in fluid system operations. Digital I/O ports provided the ability to actuate high and low level alarms and to sense the on/off status of external equipment. A number of solid state relays permitted switching of high-load 120 or 240 volt devices. Analog interfaces included 0–10 volt and 4–20 ma inputs for reading external transducers (e.g. corrosion probes, flow meters, etc.). A 4–20 ma output was provided for the control of variable speed external devices.

The example instrument was configured for fluorescence measurements and set up in an environmental chamber. The analysis and reference xenon flash lamps were flashed alternately at a rate of 5 Hz. A temperature-stable sample was produced by placing a diffuse reflectance standard in a steel cap, and attaching the cap to the end of the fluorescence probe. To reduce light intensity to a measurable level, neutral density filters were placed in the analysis and reference lamp housings.

Figure 4:
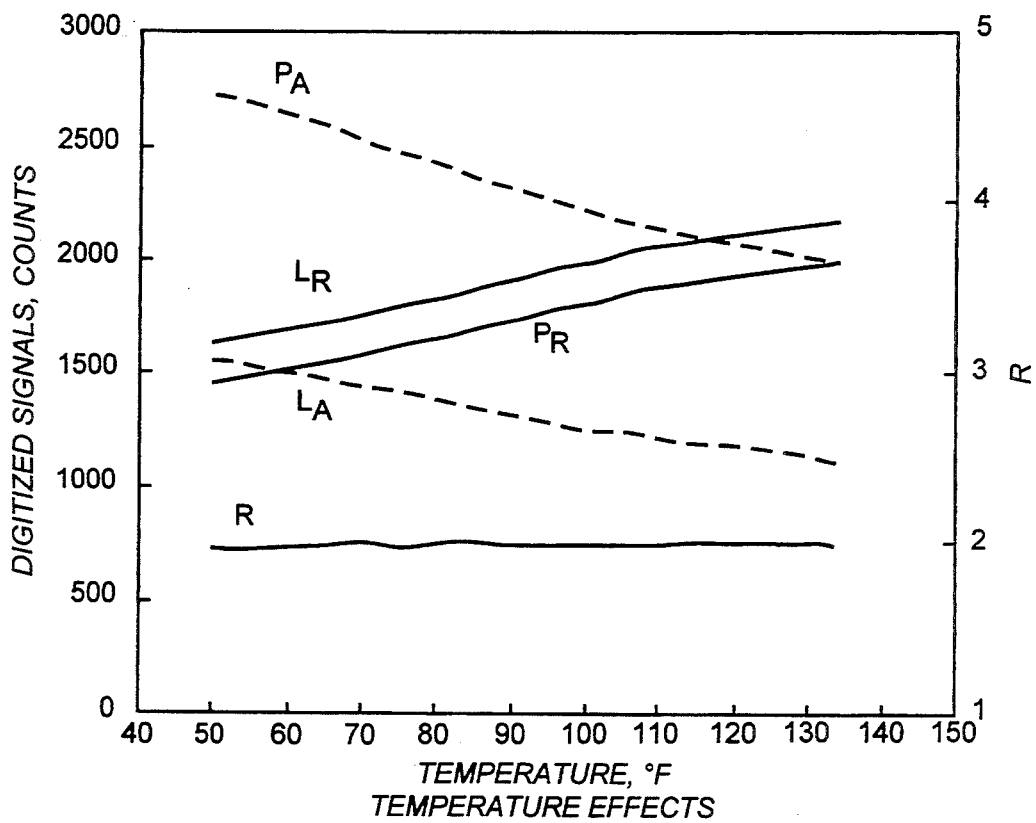
FIG. 4 is a graph showing the effect of temperature on the subject invention.

To assess the effect of temperature on instrumental response, measurements were taken over an 8 hour period, as the chamber temperature was adjusted from 50 F. to 134 F. Data was logged at intervals of 20 minutes. Results are shown in FIG. 4. Each data point represents the average of 6000 readings taken during the 20 minute interval. The analysis photomultiplier signal, $P_A$, decreased 28% over the 84 F. temperature rise. The analysis photodiode signal, $L_A$, also decreased 28%. The reference signals, $P_R$ and $L_R$ behaved in the opposite manner, each increasing 27% over the full temperature range. The different signal trends of the two optical channels are due to the fact that two different types of flash lamp power supplies were used. A high output power supply was used in the analysis channel to achieve as much fluorescence sensitivity as possible. A low output power supply was used in the reference channel, because only a small light level was required to yield adequate reference signals. The two supplies had opposite temperature coefficients, which resulted in diverging lamp intensities as temperature increased. Regardless of the reason for the drift in the raw signals, the dimensionless response parameter, R, computed with Equation 1, remained essentially constant over the entire temperature range. Therefore, analytical accuracy should not be affected by the large daily and seasonal temperature swings that occur in many industrial environments.

Figure 5:
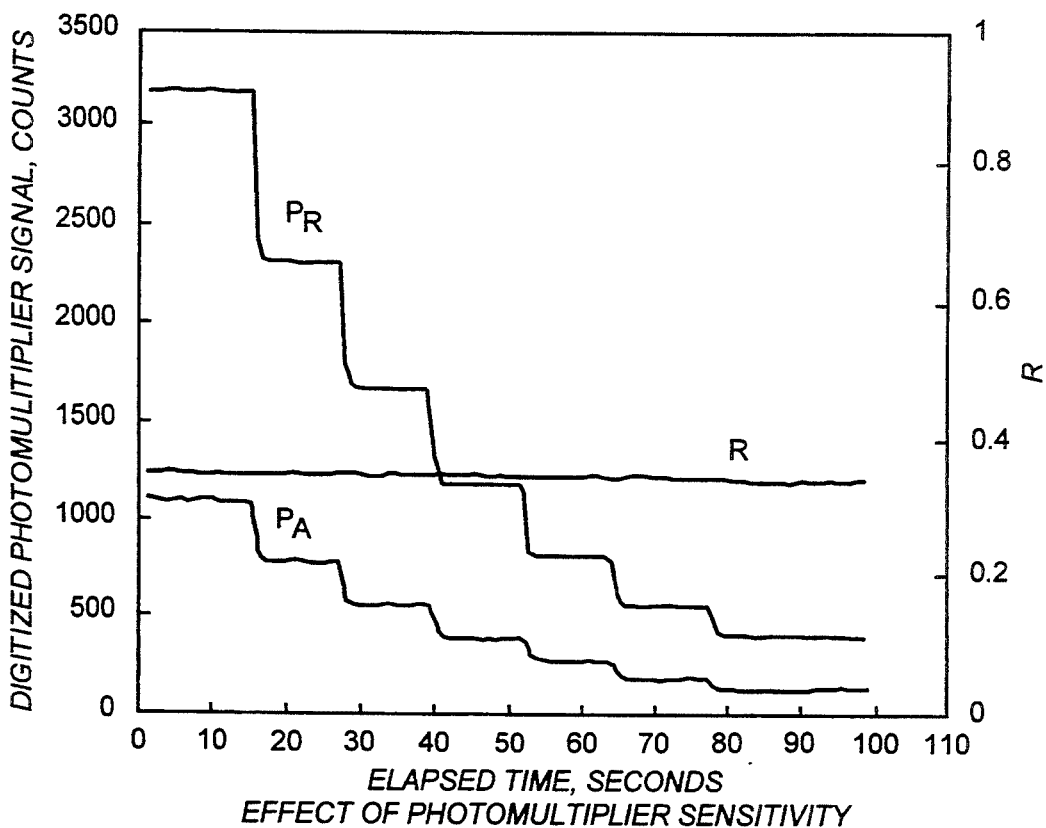
FIG. 5 is a graph showing the effect of photomultiplier sensitivity on the response of the subject invention.

To demonstrate that R effectively compensates for drastic changes in photomultiplier sensitivity, measurements were taken as applied voltage was adjusted from $-1200$ V to $-910$ V. Temperature was held constant at 95 F. Results are shown in FIG. 5. Although $P_A$ and $P_R$ were reduced to one eighth of their initial values, R again remained constant.

Figure 6:
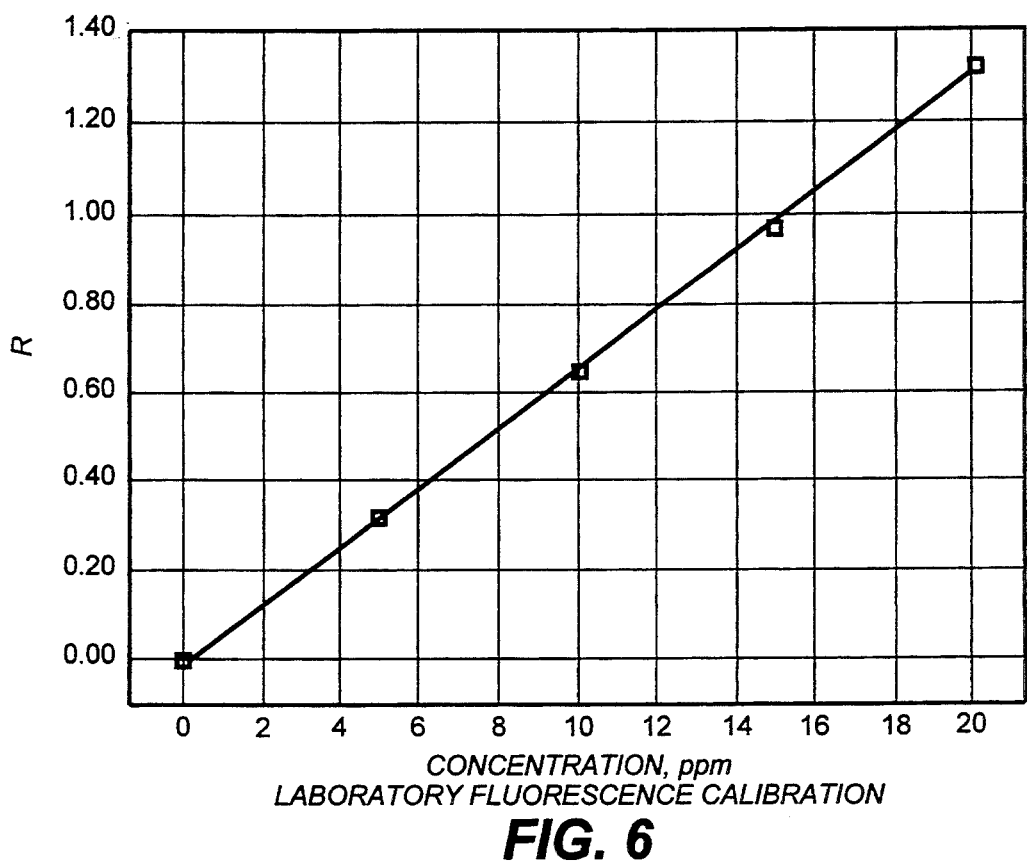
FIG. 6 is a graph showing laboratory fluorescence calibration.
Figure 7:
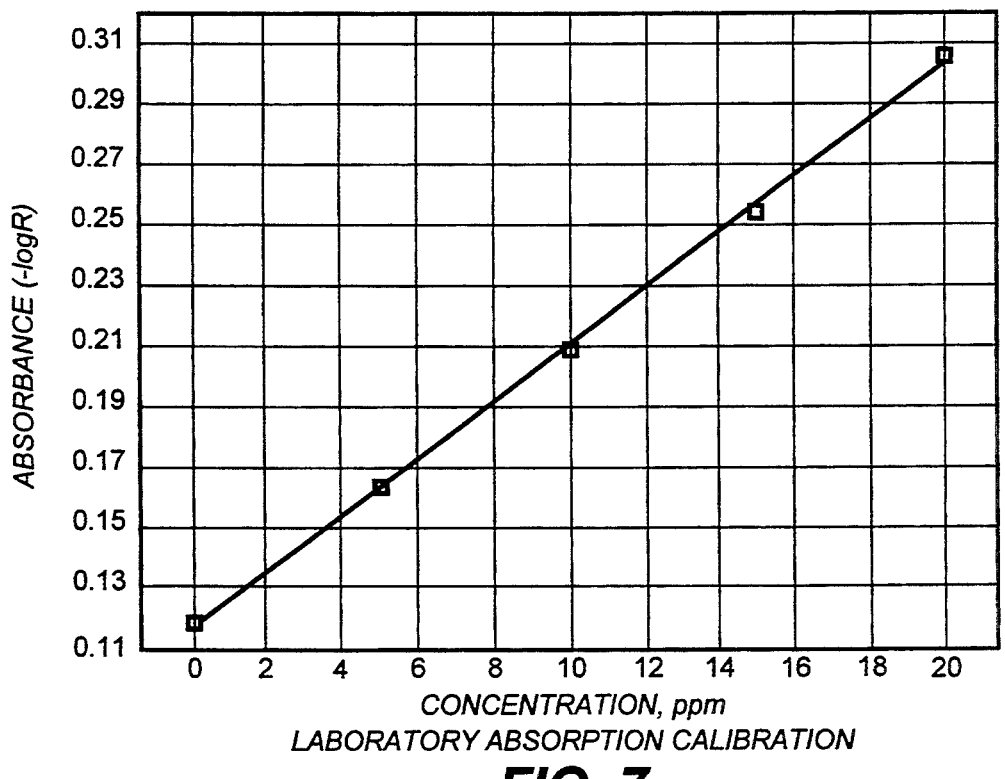
FIG. 7 is a graph showing laboratory absorption calibration.

Like all photometric instruments, the example instrument described herein must be calibrated before its response can be converted to chemical concentration. The laboratory and field calibrations described below were carried out with a water soluble, quaternary amine corrosion inhibitor that is typically used in oilfield water systems at dosages of up to 20 ppm. To evaluate the spectroscopic variability of this inhibitor, eleven separate production batches were obtained from the manufacturer. Each batch was diluted to 20 ppm in deionized water. Fluorescence measurements were taken with a commercial spectrofluorometer, using an excitation wavelength of 340 nm and an emission wavelength of 430 nm. Results are shown in FIG. 6. The relative fluorescence intensity from these samples varied from 0.91 to 1.38. This variability is hardly surprising, since chemical treating products are not usually manufactured to spectroscopic specifications. Re-calibration would therefore be advisable every time a new chemical batch is received.

Figure 8:
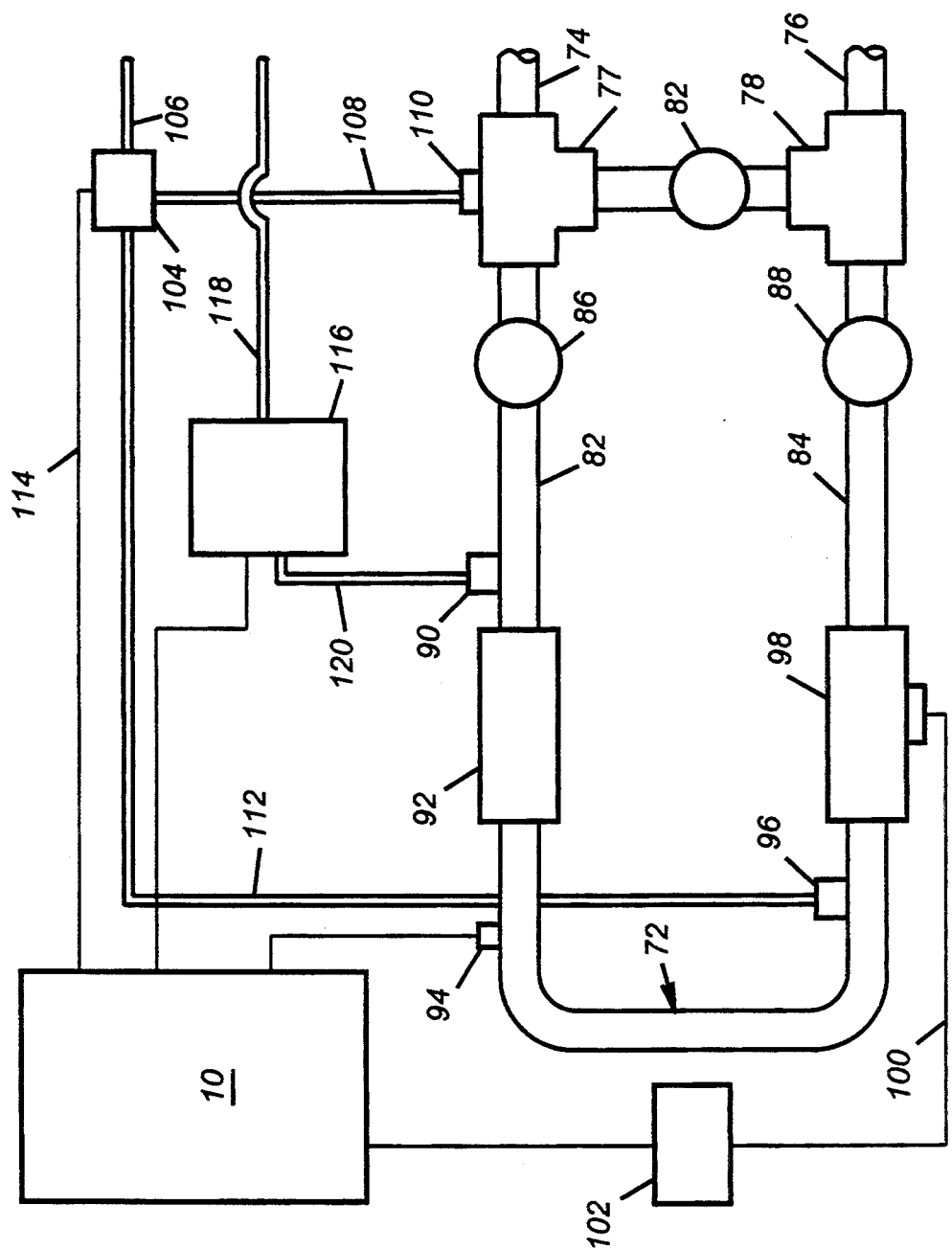
FIG. 8 is a schematic diagram of a field flow system incorporating the present invention.

Fluorescence and absorption calibration curves were generated in the laboratory by immersing the probes (described above) in standard solutions of the corrosion inhibitor dissolved in tap water. For fluorescence measurements, an excitation wavelength of 340 nm was isolated by placing an interference filter in the analysis channel lamp housing. An emission wavelength of 430 nm was isolated by an interference filter in front of the photomultiplier. Both filters had a bandpass of 10 nm. Instrumental response, R, was averaged for 20 seconds (100 analysis and reference flashes) after placing the probe in each standard solution. As shown in FIG. 6, the calibration curve was linear with a zero intercept. Absorption measurements were made at 280 nm (also isolated by a 10 nm bandpass interference filter in the analysis lamp housing). No filter was used in the photomultiplier housing. Absorption response, $-\log R$, was averaged over 20 seconds and plotted versus concentration. As shown in FIG. 8, the absorption curve was also linear up to 20 ppm. The curve has a non-zero intercept because the measurement was not referenced to a tap water blank.

Figure 9:
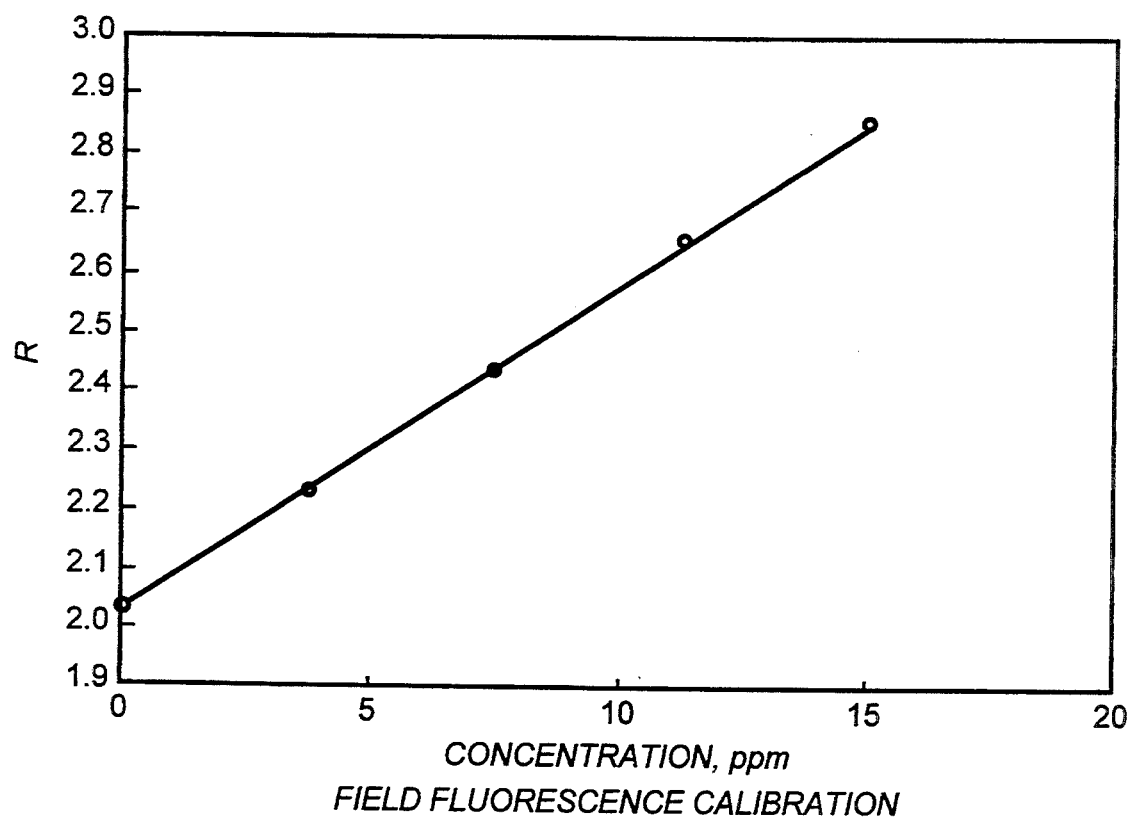
FIG. 9 is a graph showing field fluorescence calibration.

The example instrument was configured for fluorescence measurements as described above (340 nm excitation, 430 nm emission), and installed in an oilfield water system bypass loop. A diagram of the installation is shown in FIG. 9. The installation was in the form of a bypass loop 72 connected to the input flow line 74 and output flow line 76 at T-junctions 77 and 78 respectively. The T-junctions were joined together by bypass pipe 80 containing valve means 82. The T-junctions also connected to respective input and output legs 82,84 of the bypass loop 72. The legs 82,84 included valve means 86,88, respectively to isolate the bypass loop 72. The input leg 82 had calibration injection port 90 downstream of static mixer 92 and probe 94 of the subject invention upstream of the static mixer 92. The output leg 84 had injection port 96 upstream of turbine flow meter 98 which was electrically connected by line 100 to converter 102 which in turn was connected to the present invention 10. Three way solenoid valve 104 was connected by pipe 106 to a chemical supply (not shown), by pipe 108 to an injection port 110 on T-junction 77, and pipe 112 to injection port 96. Solenoid valve 104 was also electrically connected to the invention by line 114. A calibration pump 116 was also connected to the chemical supply by pipe 118 and by pipe 120 to injection port 90. Electrical line 122 connected the pump to the subject invention.

The loop 72 was made from uncoated steel pipe with an inner diameter of 7.6 cm. Ground water flowed through the loop at a nominal rate of 2500 bbl/D. The same corrosion inhibitor used in the lab test was injected through the solenoid-actuated, 3-way valve 104 through port 90 which was approximately 1.2 m upstream of the fluorescence probe 94. The static mixer 92 was placed in the line 82 to completely disperse the chemical before it reached the probe 94. The solenoid valve 104 was controlled by one of the example instrument's solid-state relays (not shown). The frequency output of a turbine flow meter 98 was converted by convertor 102 to current and monitored by the example instrument's 4–20 ma input. A variable-speed peristaltic calibration pump 116 was connected to one of the instrument's dc drivers (also not shown) so that it could be activated by the example instrument's operating program.

The calibration pump 116 was used to determine the shape of the calibration curve, and to carry out periodic auto-calibrations during normal monitoring. An initial calibration curve was determined by measuring instrumental response while pumping the inhibitor into the system at several rates. As shown in FIG. 8, R increased linearly from 2.05 to 2.85 as concentration increased from 0 to 15 ppm. The non-zero intercept was due to the presence of naturally occurring fluorophores in the field water.

Since the calibration curve was perfectly linear, it was decided to perform automatic calibrations with only zero and full-scale measurements. The calibration pump 116 was pre-set to deliver 8 mL of inhibitor at 4.1 mL/min when actuated by the example instrument. This rate corresponded to a full-scale concentration of approximately 15 ppm. The example instrument was programmed to carry out the following auto-calibration sequence:

1. Energize the solenoid valve 104 thereby switching chemical injection from port 110 to port 96 downstream of the probe 94.
2. Delay 60 seconds to establish a concentration of 0 ppm.
3. Measure $R_0$ for 20 seconds and average the results.
4. Trigger the calibration pump 116.
5. Delay 30 seconds to allow the calibration pump rate, $F_{fs}$, to stabilize.
6. Measure $R_{fs}$ and water flow rate, $F_w$, for 20 seconds, and average both results.
7. Compute the actual full-scale concentration, $C_{fs}$, in ppm by $$C_{fs} = 9.1 \times 10^3 \times F_{fs}/F_w \qquad (2)$$

8. Compute the calibration slope, m, by $$m = (R_{fs} - R_0)/C_{fs} \qquad (3)$$

9. De-energize the solenoid valve 104 thereby returning chemical injection from port 96 to port 110 upstream of the probe 94.
10. Delay 60 seconds to allow the normal treating concentration to stabilize and resume normal monitoring.

Chemical concentration, C, is determined by $$C = (R - R_0)/m \qquad (4)$$

To determine the reliability of this auto-calibration scheme, the sequence was repeated once an hour for 7 hours. As shown in Table 1, calibration slopes, m, and intercepts, $R_0$, were very reproducible. Also shown are the inhibitor concentrations that would result from an R value of 2.45, which is the average response obtained above for a chemical concentration of 7.5 ppm. The resulting concentrations averaged 7.5±0.2 ppm (±σ, 95% confidence).

TABLE 1

| Run No. | Slope (m) | Intercept ($R_0$) | Concentration[1] (ppm) |
|---|---|---|---|
| 1 | 0.0533 | 2.05 | 7.5 |
| 2 | 0.0534 | 2.05 | 7.5 |
| 3 | 0.0529 | 2.06 | 7.4 |
| 4 | 0.0530 | 2.05 | 7.5 |
| 5 | 0.0529 | 2.05 | 7.6 |
| 6 | 0.0531 | 2.06 | 7.3 |
| 7 | 0.0534 | 2.05 | 7.5 |
| Average | 0.0531 | 2.05 | 7.5 |
| σ, 95% conf.[2] | 0.0004 | 0.01 | 0.2 |

[1]Computed assuming R = 2.45
[2]Standard deviation

The present invention has been described by way of non limiting example and may be subject to many modifications and changes without departing from the spirit or essential characteristics thereof. The described embodiments should therefore be considered in all respects as being illustrative and not restrictive of the scope of the invention as defined by the appended claims.

We claim:

1. An optical system for analysis of a fluid sample comprising:
   at least an analysis light source and a reference light source;
   means controlling said light sources to emit light pulses in sequence;
   probe means adapted to be positioned in close proximity to the fluid sample to be analyzed;
   first and second photodetector means, said second photodetector means having a first portion response only to said analysis light source and a second portion responsive only to said reference light source;
   means coupling output from said analysis light source to said probe means via a first analytical path, coupling light collected by said probe means to said first photodetector means via said first analytical path, coupling output from the reference light source to both said first and second photodetector means via respective first and second reference paths and coupling output from the analysis light source to said second photodetector means via a second analytical path; and
   means to integrate output from said first and second photodetector means to compare the sensed light from said probe means and reference light to analyze the sample wherein the start of the integration period is enabled when the output of said second photodetector means exceeds a constant threshold level.

2. An optical photometry system according to claim 1 wherein said analysis and reference light sources are substantially identical.

3. An optical photometry system according to claim 1 further comprising:
   filter means limiting light output from said light sources to ultraviolet ranges.

4. An optical photometry system according to claim 1 further comprising:
   filter means limiting light output from said light sources to visible spectral ranges.

5. An optical photometry system according to claim 1 further comprising filter means limiting output from said light sources to near infrared.

6. An optical photometry system according to claim 1 wherein said light sources are selected from the group consisting of xenon flash lamps, pulsed lasers, pulsed diode lasers, pulsed light emitting diodes and continuous light sources pulsed with electronic or mechanical choppers or shutters.

7. An optical photometry system according to claim 1 wherein both said photodetector means respond to wavelengths of light emitted from said analysis and reference light sources and have a response time less than the period of both of the analysis and reference light source pulses.

8. An optical photometry system according to claim 1 wherein each said photodetector means is selected from the group consisting of avalanche photodiodes, PIN photodiodes, vacuum phototubes and photomultiplier tubes.

9. An optical photometry system according to claim 1 wherein said probe means is formed by a free end of an optical fiber cable means.

10. An optical photometry system according to claim 1 further comprising a plurality of analysis light sources and a like plurality of probe means, each of said plurality of probe means extending to a respective sample to be analyzed and each of said plurality of analysis light sources being optically coupled to a respective probe means whereby multiple samples can be monitored by a single photometry system.

11. An optical photometry system according to claim 1 wherein said system is capable of making absorption, fluorescence reflectance measurements, and light scattering at selected wavelengths in the ultraviolet through the near infrared ranges.

12. A method for performing analysis of a fluid sample with an optical photometry system comprising the steps of:
   triggering an analysis light source to emit a brief analysis light pulse;
   filtering a first portion of said analysis light pulse to a wavelength appropriate for the analysis;
   transmitting said filtered analysis light pulse to a probe means directed at the fluid sample to be analyzed;
   collecting residual light transmitted through or emanating from said sample by said probe and transmitting said residual light to a first photodetector means;
   generating a first time varying electronic signal from the action of said residual light on said first photodetector means;
   transmitting a second portion of said analysis light pulse to a second photodetector means;
   generating a second time varying electronic signal from the action of said second portion of said analysis light pulse on said second photodetector means;
   generating a first and second integrated signal by simultaneously integrating said first and second time varying electronic signals with a dual-channel integrator, wherein the start of the integration period is enabled when the output of said second photodetector means equals a constant threshold level;
   storing said first and second integrated signals in separate sample-and-hold circuits;
   generating a first and second stored numerical value by digitizing said first and second integrated signals and storing said digitized signals in digital memory;

triggering a reference light source to emit a brief reference light pulse;

transmitting a first portion of said reference light pulse to said first photodetector means and transmitting a second portion of said reference light pulse to said second photodetector means;

generating a third time varying electronic signal from the action of said first portion of said reference light pulse on said first photodetector means and generating a fourth time varying electronic signal from the action of said second portion of said reference light pulse on said second photodetector means;

generating a third and fourth integrated signal by simultaneously integrating said third and fourth time varying electronic signals with a dual-channel integrator, wherein the start of the integration period is enabled when the output of said second photodetector means equals a constant threshold level;

storing said third and fourth integrated signals in separate sample-and-hold circuits;

generating a third and fourth stored numerical value by digitizing said third and fourth integrated signals and storing said digitized signals in digital memory; and comparing said first, second, third and fourth stored numerical values whereby the analysis of said sample can be determined.

* * * * *